US012599640B2

(12) United States Patent
Wu et al.

(10) Patent No.: US 12,599,640 B2
(45) Date of Patent: Apr. 14, 2026

(54) *LACTOBACILLUS PLANTARUM* ZUST49 AND BACTERIAL AGENT, AND USE THEREOF

(71) Applicant: ZHEJIANG UNIVERSITY OF SCIENCE AND TECHNOLOGY, Zhejiang (CN)

(72) Inventors: Yuanfeng Wu, Zhejiang (CN); Chunmin Jiang, Zhejiang (CN); Yao Zhang, Zhejiang (CN); Ligen Zou, Zhejiang (CN); Zisheng Luo, Zhejiang (CN); Xinjie Song, Zhejiang (CN); Juan Sun, Zhejiang (CN); Quanmin Ma, Zhejiang (CN); Xuan Zhu, Zhejiang (CN); Sabir Z. Nishanbaev, Zhejiang (CN)

(73) Assignee: ZHEJIANG UNIVERSITY OF SCIENCE AND TECHNOLOGY, Zhejiang (CN)

( * ) Notice: Subject to any disclaimer, the term of this patent is extended or adjusted under 35 U.S.C. 154(b) by 408 days.

(21) Appl. No.: 18/337,437

(22) Filed: Jun. 20, 2023

(65) Prior Publication Data

US 2024/0374661 A1     Nov. 14, 2024

(30) Foreign Application Priority Data

May 9, 2023    (CN) ......................... 202310533235.6

(51) Int. Cl.
| | |
|---|---|
| *A61K 35/747* | (2015.01) |
| *A61K 9/48* | (2006.01) |
| *A61K 31/7028* | (2006.01) |
| *A61K 35/00* | (2006.01) |
| *A61K 36/31* | (2006.01) |
| *C12N 1/205* | (2026.01) |
| *C12R 1/25* | (2006.01) |

(52) U.S. Cl.
CPC .......... *A61K 35/747* (2013.01); *A61K 9/4808* (2013.01); *A61K 9/4858* (2013.01); *A61K 9/4866* (2013.01); *A61K 9/4875* (2013.01); *A61K 31/7028* (2013.01); *A61K 36/31* (2013.01); *C12N 1/205* (2021.05); *A61K 2035/115* (2013.01); *C12R 2001/25* (2021.05)

(58) Field of Classification Search
None
See application file for complete search history.

(56) References Cited

FOREIGN PATENT DOCUMENTS

WO    WO-2020198808 A1 *  10/2020    ............. A61K 35/60

* cited by examiner

*Primary Examiner* — Jana A Hines
*Assistant Examiner* — Khatol S Shahnan Shah
(74) *Attorney, Agent, or Firm* — JCIPRNET

(57)               ABSTRACT

The present disclosure discloses a *Lactobacillus plantarum* ZUST49 and a bacterial agent, and use thereof, and belongs to the technical field of microorganisms. An aspect of the present disclosure provides a *Lactobacillus plantarum* ZUST49 and a bacterial agent containing the *Lactobacillus plantarum* ZUST49, and another aspect provides use of the *Lactobacillus plantarum* ZUST49 and the bacterial agent containing the *Lactobacillus plantarum* ZUST49. The *Lactobacillus plantarum* ZUST49 of the present disclosure may convert glucoraphanin into sulforaphane, especially in a human or animal intestinal environment. After an enteric probiotic preparation prepared from the strain of the present disclosure is orally taken, the *Lactobacillus plantarum* ZUST49 may efficiently convert the glucoraphanin into the sulforaphane in an intestinal tract, which not only solves a problem that stability of the sulforaphane cannot be improved in the prior art, but also effectively exerts a probiotic effect.

8 Claims, 4 Drawing Sheets

Specification includes a Sequence Listing.

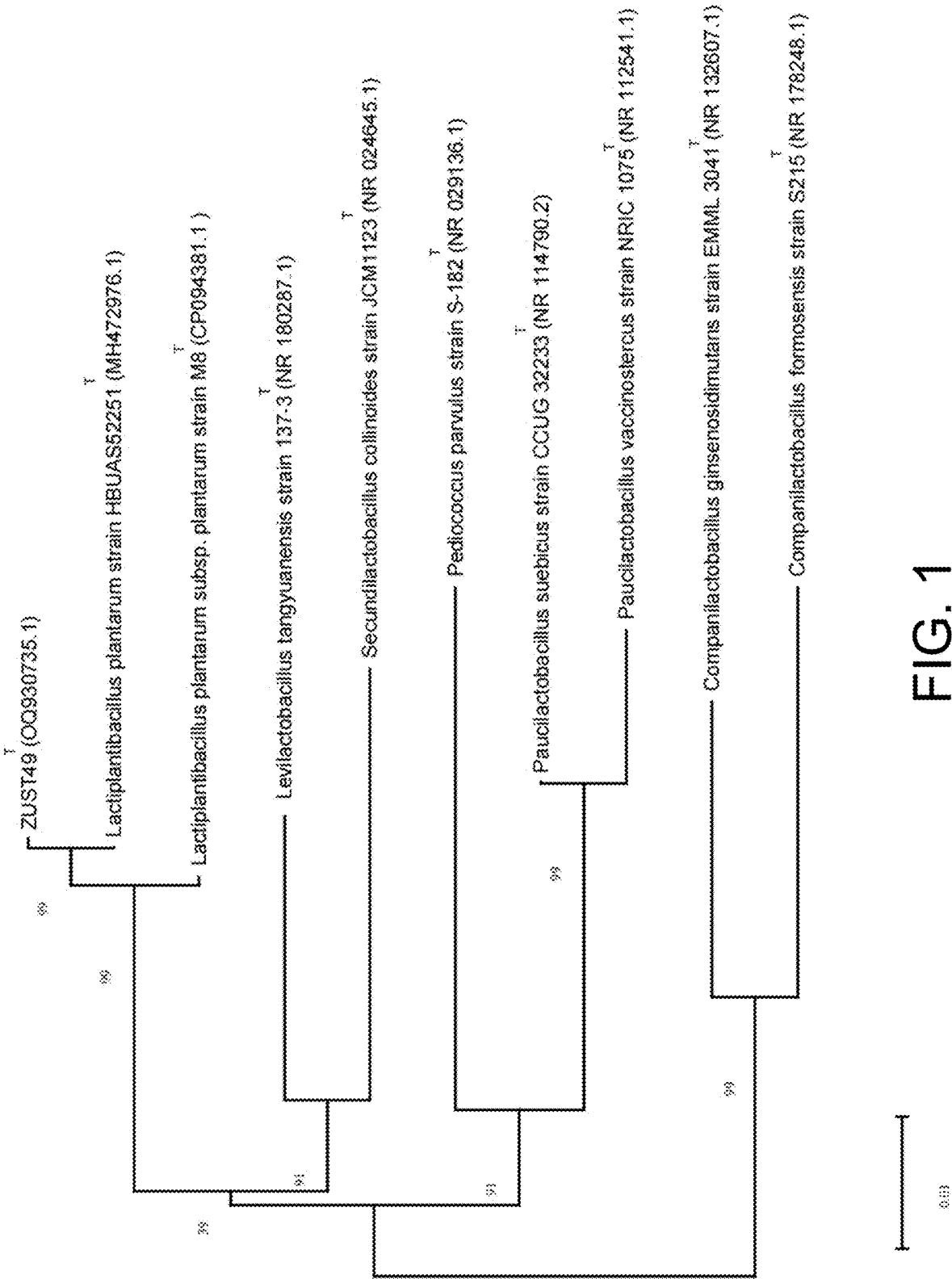

ZUST49 (OQ930735.1)

Lactiplantibacillus plantarum strain HBUAS52251 (MH472976.1)

Lactiplantibacillus plantarum subsp. plantarum strain M8 (CP094381.1 )

Levilactobacillus tangyuanensis strain 137-3 (NR 180287.1)

Secundilactobacillus collinoides strain JCM1123 (NR 024645.1)

Pediococcus parvulus strain S-182 (NR 029136.1)

Paucilactobacillus suebicus strain CCUG 32233 (NR 114790.2)

Paucilactobacillus vaccinostercus strain NRIC 1075 (NR 112541.1)

Companilactobacillus ginsenosidimutans strain EMML 3041 (NR 132607.1)

Companilactobacillus formosensis strain S215 (NR 178248.1)

FIG. 1

LACTOBACILLUS PLANTARUM ZUST49 AND BACTERIAL AGENT, AND USE THEREOF

CROSS-REFERENCE TO RELATED APPLICATION

This application claims the priority benefit of China application no. 202310533235.6, filed on May 9, 2023. The entirety of each of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Jun. 12, 2023, is named 135150_SEQUENCELISTING and is 3,510 bytes in size.

BACKGROUND OF THE INVENTION

1. Technical Field

The present disclosure belongs to the technical field of microorganisms, and specifically relates to a *Lactobacillus plantarum* ZUST49 and a bacterial agent, and use thereof.

2. Background Art

Sulforaphane (1-isothiocyanato-4-methylsulfonylbutane) is one of the strongest anticancer components in vegetables due to its inhibition of phase I enzymes, activation of drug metabolizing enzymes and transcription factor NF-E2 related factor (Nrf2), and inhibition of nuclear factor kappa B (NF-κB) and histone deacetylases, etc. Animal experiments demonstrated that sulforaphane had various activities, such as cancer prevention and inhibition, anti-oxidation, and immunity regulation. Recent studies have shown that sulforaphane also has a good therapeutic effect on autism.

Sulforaphane is obtained from the enzymolysis of glucoraphanin (4-methylsulfinylbutenyl glucosinolate) by myrosinase. Studies have shown that glucoraphanin exists in brassica vegetables such as broccoli, cabbage, and Chinese kale, with the highest content in broccoli. When plants containing glucoraphanin, such as broccoli, are cut or nibbled, glucoraphanin will be enzymatically hydrolyzed by the myrosinase contained in the plants themselves to produce sulforaphane.

In terms of stability, glucoraphanin is very stable, while myrosinase and sulforaphane are not. When broccoli is cooked, myrosinase becomes inactive, which prevents the production of sulforaphane. The extracted sulforaphane is also easy to degrade even in a refrigeration environment, which limits its application in medicine and health products. Therefore, there are very few health-care or medical products containing isothiocyanate on the market, such as SFX, and Prostaphane®, in a form of microencapsulated sulforaphane. Due to the poor stability of sulforaphane, these products need to be transported and stored under cold chain conditions, and have a relatively short shelf life (less than or equal to 1 year). In order to solve these difficulties, it is urgent to screen some probiotics capable of exercising the function of myrosinase, and prepare probiotic preparations to degrade glucoraphane in vivo and generate sulforaphane.

The dosage form is of great significance to the activity of probiotics. The common dosage forms of probiotic products are liquid preparation, tablet, powder, and capsule. For liquid preparations, there is a problem that probiotics cannot survive for a long time. Because tablets require high temperature drying and are susceptible to moisture during processing, the number of viable probiotics in tablets is usually relatively low. Most powders are freeze-dried probiotic powders processed by low-temperature freeze-drying; therefore, it is difficult to control the water temperature when the powders are brewed with warm water, which makes it difficult to guarantee the activity of probiotics. The packaging using traditional gelatin capsules can effectively isolate oxygen and the capsules dissolve faster than tablets, but the capsules generally disintegrate in the stomach, making it difficult for the probiotics inside to be protected. In contrast, enteric capsules have the advantages of gastric acid resistance and intestinal dissolution, and, therefore, can better protect the probiotics from being digested before reaching the intestinal tract.

SUMMARY OF THE INVENTION

In view of the problems in the prior art, the present disclosure is intended to design and provide technical solutions of a *Lactobacillus plantarum* ZUST49 and a bacterial agent, and use thereof.

The present disclosure specifically adopts the following technical solutions:

A first aspect of the present disclosure provides a *Lactobacillus plantarum* ZUST49. The strain has been deposited in China General Microbiological Culture Collection Center (CGMCC) located at No. 3, Yard 1, West Beichen Road, Chaoyang District, Beijing, Institute of Microbiology of Chinese Academy of Sciences on Mar. 23, 2023, and has the deposit number of CGMCC No. 26892.

A second aspect of the present disclosure provides a bacterial agent containing the *Lactobacillus plantarum* ZUST49.

Furthermore, the content of the *Lactobacillus plantarum* ZUST49 in the bacterial agent is ≥1×10⁵ CFU/g.

Furthermore, the bacterial agent further contains glucoraphanin and/or a raw material containing the glucoraphanin.

Furthermore, in the bacterial agent, the raw material containing the glucoraphanin is one of dried broccoli, cabbage, and cabbage mustard or a mixture thereof.

Furthermore, the content of the glucoraphanin in the bacterial agent is 0.2-10 mg/g.

A third aspect of the present disclosure provides use of the *Lactobacillus plantarum* ZUST49 or any one of the bacterial agent in converting the glucoraphanin into sulforaphane.

A fourth aspect of the present disclosure provides use of the *Lactobacillus plantarum* ZUST49 or any one of the bacterial agent in converting the glucoraphanin into sulforaphane in a human or animal intestinal environment.

A fifth aspect of the present disclosure provides use of the *Lactobacillus plantarum* ZUST49 or any one of the bacterial agent in the preparation of an enteric probiotic preparation.

Furthermore, the enteric probiotic preparation is for providing sulforaphane to a human body.

Compared with the prior art, the present disclosure has the following beneficial effects:

The *Lactobacillus plantarum* ZUST49 of the present disclosure may convert glucoraphanin into sulforaphane, especially in a human or animal intestinal environment. After an enteric probiotic preparation prepared from the strain of the present disclosure is orally taken, the *Lactobacillus plantarum* ZUST49 may efficiently convert the glucoraphanin into the sulforaphane in an intestinal tract, which not only solves a problem that stability of the sulforaphane cannot be improved in the prior art, but also effectively exerts a probiotic effect.

BRIEF DESCRIPTION OF THE DRAWINGS

FIG. 1 is a 16S rRNA phylogenetic tree of *Lactobacillus plantarum* ZUST49;

DETAILED DESCRIPTION OF THE EMBODIMENTS

Figure 2:
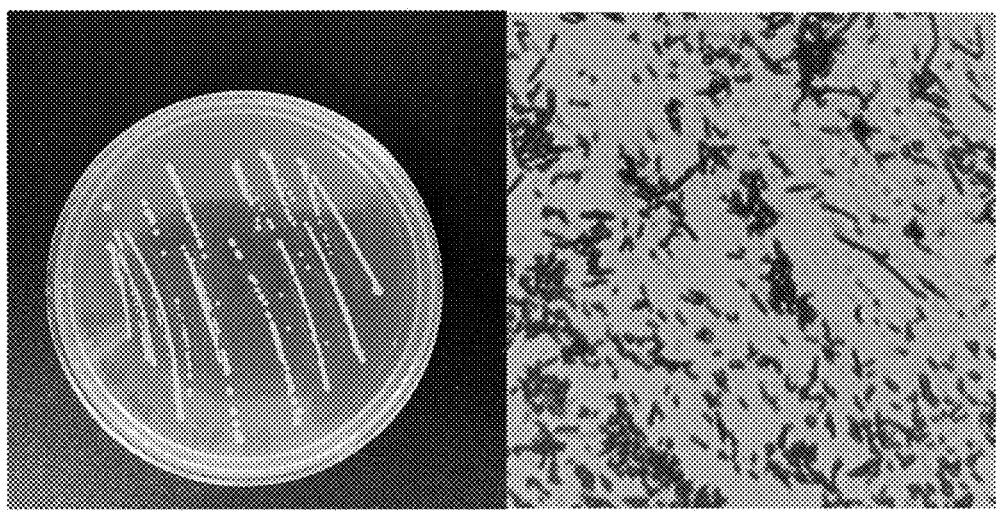
FIG. 2 shows characteristic graphs of colony morphology and microscopic morphology of *Lactobacillus plantarum* ZUST49.

The present disclosure will be further described below with reference to the accompanying drawings and embodiments, but is not thereby limited to the scope of the described examples. The experimental methods in the following examples without specified specific conditions should be selected according to conventional methods and conditions, or according to instructions of products.

Example 1 Separation, Screening, and Identification of *Lactobacillus plantarum* ZUST49

(1) Culture Medium:

MRS culture medium: 10 g of peptone, 8 g of beef powder, 4 g of yeast powder, 20 g of glucose, 2 g of dipotassium phosphate, 2 g of diammonium hydrogen citrate, 5 g of sodium acetate, 0.2 g of magnesium sulfate, 0.04 g of manganese sulfate, 1 mL of Tween 80, and 15 g of agar were weighed and added to 1,000 mL of distilled water. The materials were heated and dissolved, a constant volume was set, a pH was adjusted to 6.0-6.4, and a high-pressure sterilization was performed at 121° C. for 15 min.

MRS liquid culture medium: no agar was added during the preparation of the MRS culture medium, other components were completely the same, and a high-pressure sterilization was performed at 121° C. for 15 min.

M17 culture medium: 5 g of soytone, 2.5 g of peptone, 2.5 g of casein peptone, 5 g of beef extract powder, 5 g of lactose, 0.5 g of sodium ascorbate, 19 g of β-sodium glycerophosphate, 0.25 g of magnesium sulfate, and 12.75 g of agar, 1,000 mL of distilled water was added, the materials were heated and dissolved, a constant volume was set, a pH was adjusted to 7.0-7.4, and a high-pressure sterilization was performed at 121° C. for 15 min.

M17 liquid culture medium: no agar was added during the preparation of the M17 liquid culture medium, other components were completely the same, and a high-pressure sterilization was performed at 121° C. for 15 min.

Crude thioglycoside culture medium: 100 g of broccoli seeds were taken and crushed into fine powder, 400 mL of distilled water was added, the material was boiled for 30 min, filtered with 3 layers of gauze to remove a residue, centrifugation was performed at 10,000 r/min for 10 min to remove a precipitate, a constant volume was set to 500 mL, and sterilization was performed at 121° C. for 30 min.

(2) Isolation and Purification of Bacterial Solution

Chinese cabbages purchased from market were shredded, seasoning and purified water were added, and the material was sealed and naturally fermented for one week. A pickled vegetable solution was immediately transferred into an anaerobic operation box. Sterile plates of the MRS, M17, and crude thioglycoside culture mediums were prepared, cooled, and solidified, and 0.1 mL of a bacterial solution was dripped by using a pipette, and ed. Types, time, and numbers of streaked culture dishes were marked, and the culture dishes were taken out after the marking was all completed, and put into a constant-temperature anaerobic incubator at 37° C. for 24 h.

After a 1st culture was completed, a single colony was picked to a corresponding liquid culture medium, types, numbers, and dates were recorded, and the culture mediums were put into the constant-temperature anaerobic incubator at 37° C. for 24 h after the recording was all completed.

(3) Screening of Strain

In a sterile operating station, a glucoraphanin solution was added to the liquid culture medium after the high-temperature sterilization via a—20 μm filter membrane to a final concentration of glucoraphanin of 1 mM, and the culture medium was sub-packaged into test tubes. 25 μL of a bacterial solution after a 2nd culture was added into the test tubes of the corresponding culture mediums by using a pipette, and the bacteria were put into a constant-temperature incubator at 37° C. for culture for 12 h. After the culture was completed, a concentration of the glucoraphanin in each test tube was measured by a glucose detection kit method, a conversion rate was calculated, and a bacterial solution with a relatively high degradation rate was screened, recorded, and numbered. A colony morphology of *Lactobacillus plantarum* ZUST49 on the MRS culture medium was milky white, smooth, and round with a bulge, and neat in edges. A microscopic morphology was in rod-like, paired or chain-like arrangements (FIG. 2).

(4) Deposit and Identification of Strain

500 μL of the bacterial solution after 2 times of the liquid culture was taken and added into 500 μL of 40% glycerol (final concentration of 20%), the materials were shaken and mixed uniformly, and the mixture was cryopreserved in a refrigerator at −20° C.

The *Lactobacillus plantarum* ZUST49 obtained by screening using a modern molecular biology identification technology was subjected to a 16S rRNA sequence identification. A sequencing result was shown in SEQ ID NO. 1 of a sequence listing. A molecular biology rapid identification was performed by a 16S rDNA gene sequence analysis method. An identification result was *Lactobacillus plantarum* with a homology similarity of 100%, and the strain was named ZUST49. A 16S rRNA phylogenetic tree of the strain was shown in FIG. 1. The strain was deposited in China General Microbiological Culture Collection Center (CGMCC) located at No. 3, Yard 1, West Beichen Road, Chaoyang District, Beijing, Institute of Microbiology of Chinese Academy of Sciences on Mar. 23, 2023, and had the deposit number of CGMCC No. 26892.

Example 2 Conversion Rate of Glucoraphanin by *Lactobacillus plantarum* ZUST49

A glucoraphanin solution was added to the MRS liquid culture medium after the high-temperature sterilization via a—20 μm filter membrane to a final concentration of glucoraphanin of 1 mM, and the culture medium was sub-packaged into test tubes. 50 μL of activated *Lactobacillus*

Figure 3:
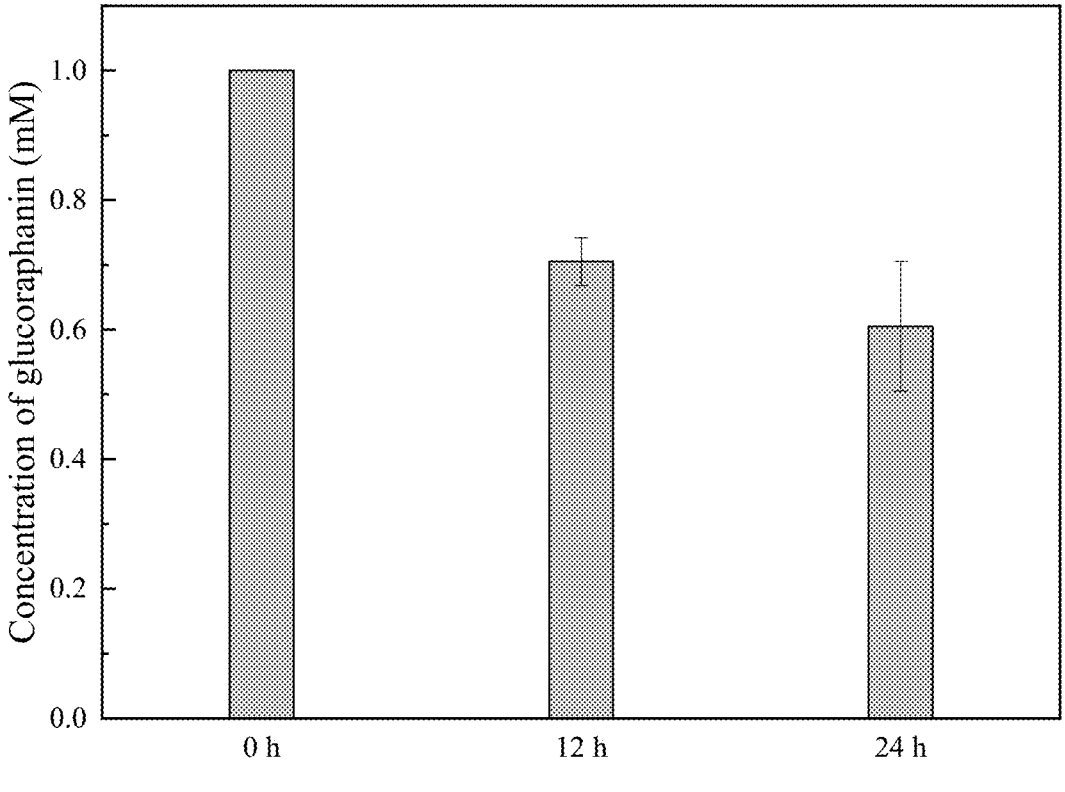
FIG. 3 shows a glucoraphanin conversion rate of *Lactobacillus plantarum* ZUST49.

*plantarum* ZUST49 solution was taken using a pipette, and added into corresponding MRS liquid culture mediums, and the liquid culture mediums were put into a constant-temperature incubator at 37° C. for culture for 12 h and 24 h respectively. After the culture was completed, a concentration of the glucoraphanin in each test tube was measured by a glucose detection kit method, a conversion rate was calculated. The result showed a highest conversion rate of the glucoraphanin of the screened strain may reach 39.5% (FIG. 3).

TABLE 1

| Conversion rate of glucoraphanin by *Lactobacillus plantarum* ZUST49 | | | |
| --- | --- | --- | --- |
| | Before fermentation | Culture for 24 h | Reduction of glucoraphanin |
| Content of glucoraphanin (mM) | 1.000 | 0.605 ± 0.10 | 0.395 |

Therefore, the conversion rate of the glucoraphanin was 39.5%.

Note:Conversion rate of glucoraphanin =

$$\frac{\text{Reduction of glucoraphanin}}{\text{Content of glucoraphanin in culture medium before fermentation}} 100\%$$

Example 3 Preparation of Enteric Capsule Containing Glucoraphanin (1) Obtaining of Bacteria The screened strain was inoculated into 30 mL of an MRS liquid culture medium at an amount of 1% (V/V), subjected to an anaerobic culture at a constant temperature of 37° C. for 24 h, and activated twice. Then the strain was inoculated into 1.50 L of the MRS liquid culture medium at an amount of 1%, subjected to an anaerobic culture at a constant temperature of 37° C. for 24 h, and centrifuged at 6,000 r/min for 20 min to obtain bacteria. The bacteria were washed twice with a PBS buffer solution.

(2) Preparation of Glucoraphanin Capsule

Glucoraphanin (100 μM), 2% of xylooligosaccharide, 4% of whey protein, and 2% of sodium alginate were mixed, the mixture was dropwise added into a 2% calcium chloride solution to form calcium alginate gel beads, stood for 30 min and placed in a 0.5% chitosan solution for immobilization, redundant chitosan was washed off, and the gel beads were placed into an ultralow-temperature refrigerator for freezing overnight at −80° C. and freeze-dried in a freeze dryer for 24 h to obtain 1.36 kg of a glucoraphanin capsule with the glucoraphanin content of 6.57 mg/g.

(3) Preparation of Bacterial Agent Capsule

The *Lactobacillus plantarum* strain ($10^{10}$ CFU/mL), 2% of xylooligosaccharide, 4% of whey protein, and 2% of sodium alginate were mixed, the mixture was dropwise added into a 2% calcium chloride solution to form calcium alginate gel beads, stood for 30 min and placed in a 0.5% chitosan solution for immobilization, redundant chitosan was washed off, and the gel beads were placed into an ultralow-temperature refrigerator for freezing overnight at −80° C. and freeze-dried in a freeze dryer for 24 h to obtain 1.31 kg of a glucoraphanin enteric capsule.

(4) Assembly of Capsule

Figure 4:
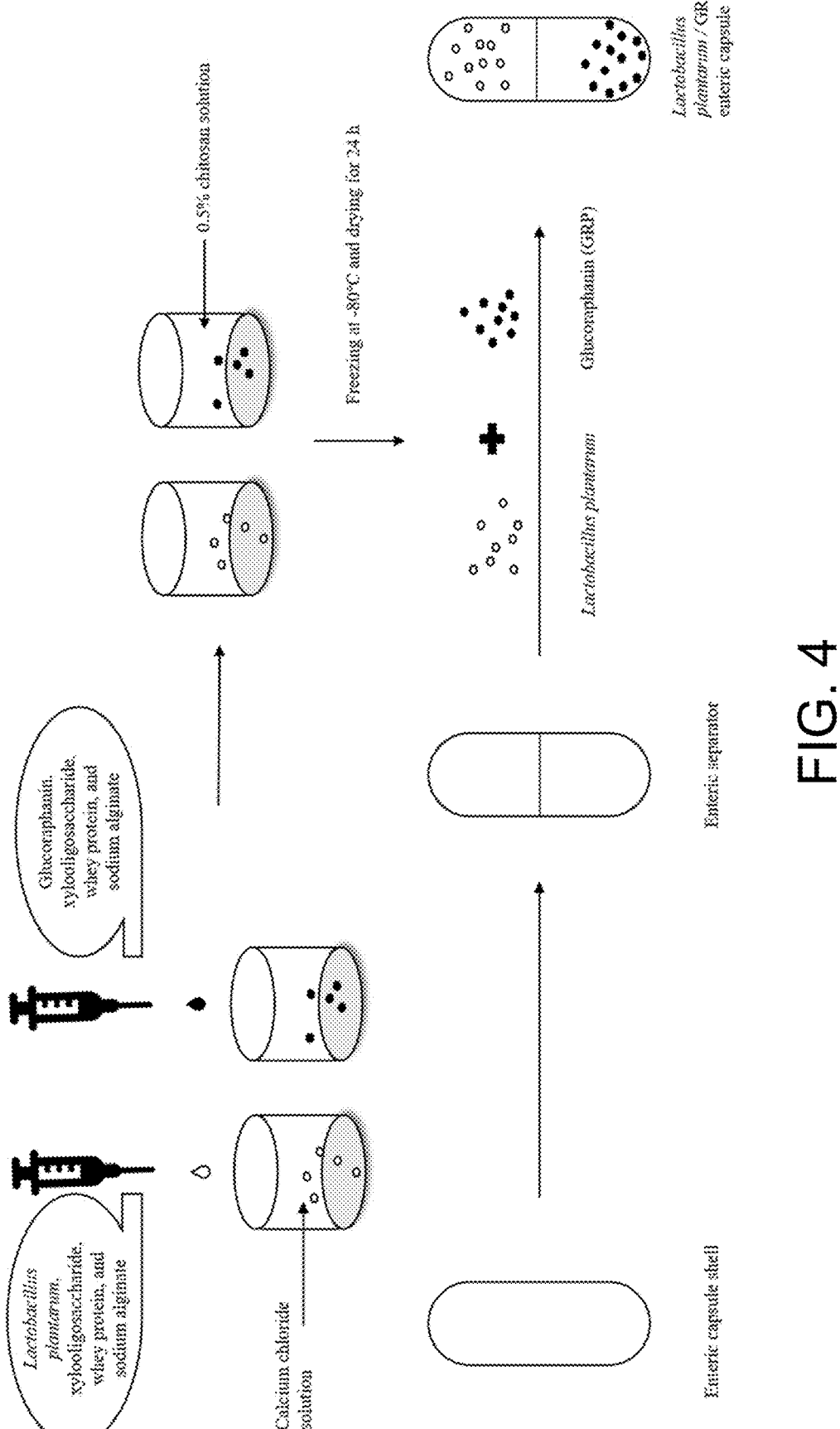
FIG. 4 is a flow chart of a manufacturing process of an enteric capsule.

Canning was performed using a semi-automatic capsule canning machine, the bacterial agent capsule and the glucoraphanin capsule were assembled to obtain 2.65 kg of a capsule containing *Lactobacillus plantarum* ZUST49 and glucoraphanin, wherein the content of ZUST49 was $8.7 \times 10^5$ CFU/g. A manufacturing process of the enteric capsule was shown in FIG. 4.

Example 4 Preparation of Enteric Capsule Containing Freeze-Dried Broccoli Powder (1) Obtaining of Bacteria The screened strain was inoculated into 30 mL of an MRS liquid culture medium according to the amount of 1% (V/V), subjected to an anaerobic culture at a constant temperature of 37° C. for 24 h, and activated twice. Then the strain was inoculated into 1.50 L of the MRS liquid culture medium according to the amount of 1%, subjected to an anaerobic culture at a constant temperature of 37° C. for 24 h, and centrifuged at 6,000 r/min for 20 min to obtain bacteria. The bacteria were washed twice with a PBS buffer solution.

(2) Preparation of Freeze-Dried Broccoli Powder 15.0 kg of broccoli buds were cleaned, drained, and cut into blocks with a size of 3 cm×3 cm. The blocks were subjected to hot-air drying in a hot-air drying box at 70° C. for 7 h, and crushed to obtain 1.65 kg of a broccoli powder with the glucoraphanin content of 0.87 mg/g.

(3) Preparation of Bacterial Agent Capsule

The *Lactobacillus plantarum* ($10^{10}$ CFU/mL), 2% of xylooligosaccharide, 4% of whey protein, and 2% of sodium alginate were mixed, the mixture was dropwise added into a 2% calcium chloride solution to form calcium alginate gel beads, stood for 30 min and placed in a 0.5% chitosan solution for immobilization, redundant chitosan was washed off, and the gel beads were placed into an ultralow-temperature refrigerator for freezing overnight at −80° C. and freeze-dried in a freeze dryer for 24 h to obtain 1.51 kg of a glucoraphanin capsule.

(4) Assembly of Capsule

Canning was performed using a semi-automatic capsule canning machine, the bacterial agent capsule and the glucoraphanin capsule were assembled to obtain 3.11 kg of a capsule containing *Lactobacillus plantarum* ZUST49 and glucoraphanin, wherein the content of ZUST49 was $6.2 \times 10^5$ CFU/g.

Example 5 Production of Sulforaphane by Feeding Mice with Enteric Capsule

Figure 5:
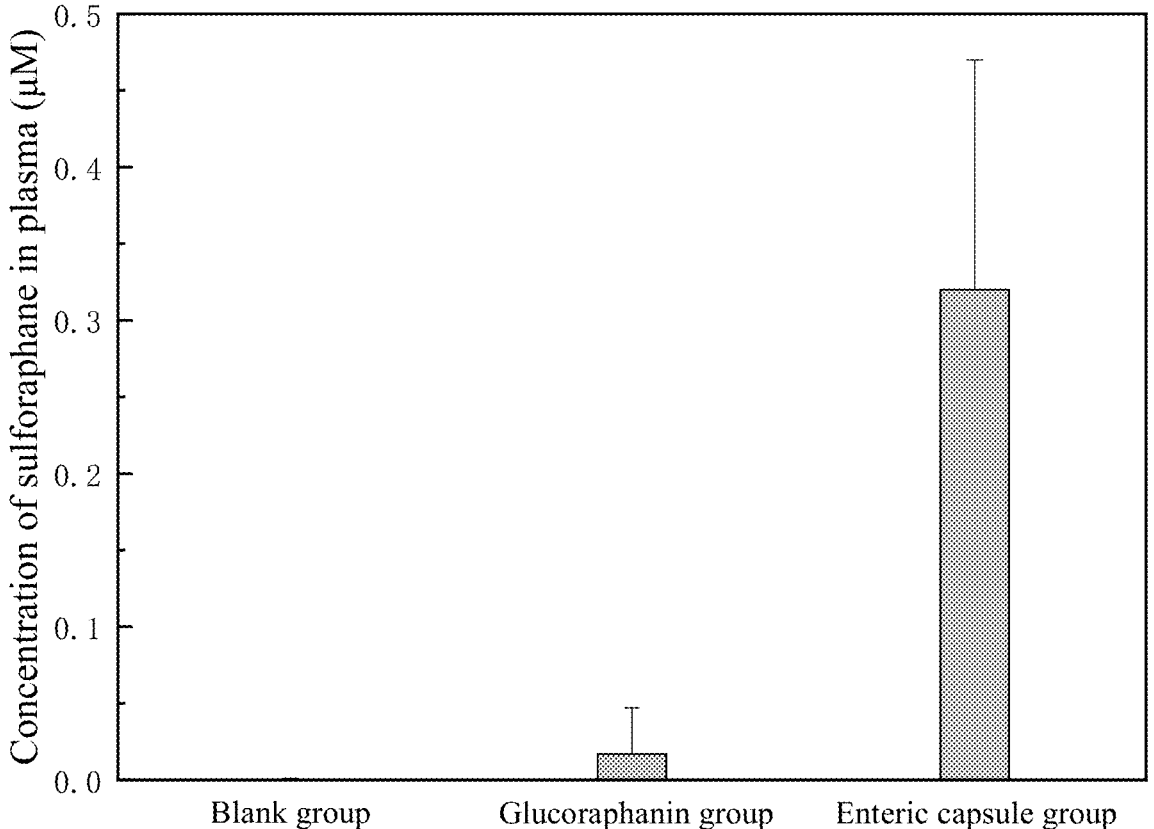
FIG. 5 shows a comparison of the content of sulforaphane in mouse plasma.

C57BL/6 male mice of 6 to 8 weeks were pre-reared for 1 week and randomly divided into an enteric capsule group, a glucoraphanin group, and a blank group. Mice in the enteric capsule group were intragastrically administered daily with an enteric capsule aqueous solution containing *Lactobacillus plantarum* ZUST49 and glucoraphanin (150 μmol of glucoraphanin/kg and ZUST49 content of $8.7 \times 10^5$ CFU/g, and prepared according to the method of example 3). The mice in the glucoraphanin group were intragastrically administrated with a glucoraphanin aqueous solution (150 μmol of glucoraphanin/kg). The mice were fed with food and water ad libitum. Food intake and weight were recorded daily. The mice were deeply anesthetized with an intraperitoneal injection of ketamine/xylazine (87 mg/mL and 13 mg/mL respectively, and 0.1 mL/100 g mice) at 0 h and 12 h (6 mice/group each time period), and put to death by cervical dislocation after blood collection by cardiac puncture. The sulforaphane content in plasma of the mice was determined by a cyclocondensation method. A result was shown in FIG. 5 and indicated that the sulforaphane content in the plasma of the mice fed with the enteric capsule reached $0.32\pm0.15$ UM, which was significantly higher than that of the glucoraphanin group ($0.017\pm0.030$ μM) and the blank group (0 μM).

Finally, it should be noted that the above examples area only intended to explain, rather than to limit, the technical solutions of the present disclosure. Although the present disclosure is described in detail with reference to the preferred example, those of ordinary skill in the art should understand that modifications or equivalent substitutions made to the technical solutions of the present disclosure without departing from the spirit and scope of the technical solutions of the present disclosure should be included within the scope of the claims of the present disclosure.

What is claimed is:

1. A method of preparing an enteric probiotic preparation, comprising:

preparing a glucoraphanin capsule comprising 100 μM of glucoraphanin;

preparing a bacterial agent capsule comprising $10^{10}$ CFU/mL of *Lactobacillus plantarum* ZUST49; and assembling the bacterial agent capsule and the glucoraphanin capsule to obtain an enteric capsule containing the *Lactobacillus plantarum* ZUST49 and the glucoraphanin, wherein the enteric probiotic preparation comprises the enteric capsule, wherein the *Lactobacillus plantarum* ZUST49 has a deposit number of CGMCC No. 26892.

2. The method according to claim 1, wherein the enteric probiotic preparation is for providing sulforaphane to a human body.

3. A method of preparing an enteric probiotic preparation, comprising:

preparing a glucoraphanin capsule comprising of glucoraphanin;

preparing a bacterial agent capsule comprising a bacterial agent; and assembling the bacterial agent capsule and the glucoraphanin capsule to obtain an enteric capsule containing the bacterial agent and the glucoraphanin, wherein the enteric probiotic preparation comprises the enteric capsule, and wherein the bacterial agent comprises *Lactobacillus plantarum* ZUST49 having a deposit number of CGMCC No. 26892.

4. The method according to claim 3, wherein the enteric probiotic preparation is for providing sulforaphane to a human body.

5. The method according to claim 3, wherein a content of the *Lactobacillus plantarum* ZUST49 in the bacterial agent is $\geq 1\times10^5$ CFU/g.

6. The method according to claim 3, wherein the bacterial agent further comprises glucoraphanin and/or a raw material containing the glucoraphanin.

7. The method according to claim 6, wherein in the bacterial agent, the raw material comprising the glucoraphanin is one of dried broccoli, cabbage, and cabbage mustard or a mixture thereof.

8. The method according to claim 6, wherein a content of the glucoraphanin in the bacterial agent is 0.2-10 mg/g.

\* \* \* \* \*

SEQUENCE LISTING

```
Sequence total quantity: 1
SEQ ID NO: 1          moltype = DNA  length = 1469
FEATURE               Location/Qualifiers
source                1..1469
                      mol_type = genomic DNA
                      organism = Lactobacillus plantarum
SEQUENCE: 1
tttgatcatg gctcaggacg aacgctggcg gcgtgcctaa tacatgcaag tcgaacgaac    60
tctggtattg attggtgctt gcatcatgat ttacatttga gtgagtggcg aactggtgag   120
taacacgtgg gaaacctgcc cagaagcggg ggataacacc tggaaacaga tgctaatacc   180
gcataacaac ttggaccgca tggtccgagc ttgaaagatg gcttcggcta tcacttttg    240
atggtcccgc ggcgtattag ctagatggtg gggtaacggc tcaccatggc aatgatacgt   300
agccgacctg agagggtaat cggccacatt gggactgaga cacggcccaa actcctacgg   360
gaggcagcag tagggaatct tccacaatgg acgaaagtct gatggagcaa cgccgcgtga   420
gtgaagaagg gtttcggctc gtaaaactct gttgttaaag aagaacatat ctgagagtaa   480
ctgttcaggt attgacggta tttaaccaga aagccacggc taactacgtg ccagcagccg   540
cggtaatacg taggtggcaa gcgttgtccg gatttattgg gcgtaaagcg agcgcaggcg   600
gttttttaag tctgatgtga aagccttcgg ctcaaccgaa gaagtgcatc ggaaactggg   660
aaacttgagt gcagaagagg acagtggaac tccatgtgta gcggtgaaat gcgtagatat   720
atggaagaac accagtggcg aaggcggctg cctggtctgt aactgacgct gaggctcgaa   780
agtatgggta gcaaacagga ttagataccc tggtagtcca taccgtaaac gatgaatgct   840
aagtgttgga gggtttccgc ccttcagtgc tgcagctaac gcattaagca ttccgcctgg   900
ggagtacggc cgcaaggctg aaactcaaag gaattgacgg gggcccgcac aagcggtgga   960
gcatgtggtt taattcgaag ctacgcgaag aaccttacca ggtcttgaca tactatgcaa  1020
atctaagaga ttagacgttc ccttcgggga catggataca ggtggtgcat ggttgtcgtc  1080
agctcgtgtc gtgagatgtt gggttaagtc ccgcaacgag cgcaaccctt attatcagtt  1140
gccagcatta agttgggcac tctggtgaga ctgccggtga caaaccggag gaaggtgggg  1200
atgacgtcaa atcatcatgc cccttatgac ctgggctaca cacgtgctac aatggatggt  1260
acaacgagtt gcgaactcgc gagagtaagc taatctctta aagccattct cagttcggat  1320
tgtaggctgc aactcgccta catgaagtcg gaatcgctag taatcgcgga tcagcatgcc  1380
gcggtgaata cgttcccggg ccttgtacac accgcccgtc acaccatgag agtttgtaac  1440
acccaaagtc ggtggggtaa ccttttagg                                    1469
```